United States Patent
Chou et al.

(10) Patent No.: US 7,671,251 B2
(45) Date of Patent: Mar. 2, 2010

(54) IN VIVO ASSAY FOR NEURITE OUTGROWTH IN ZEBRAFISH AND ITS APPLICATION IN DRUG SCREENING

(75) Inventors: Chih-Ming Chou, Taipei (TW); I-Ching Lu, Taipei (TW); Gen-Der Chen, Taipei (TW); Chioh-Yueh Chen, Taipei (TW); Chang-Jen Huang, Taipei (TW)

(73) Assignee: Academia Sinica, Taipei (TW)

( * ) Notice: Subject to any disclaimer, the term of this patent is extended or adjusted under 35 U.S.C. 154(b) by 608 days.

(21) Appl. No.: 11/327,263

(22) Filed: Jan. 6, 2006

(65) Prior Publication Data

US 2006/0179506 A1 Aug. 10, 2006

Related U.S. Application Data

(60) Provisional application No. 60/642,064, filed on Jan. 7, 2005.

(51) Int. Cl.
*A01K 67/027* (2006.01)
*G01N 33/00* (2006.01)
(52) U.S. Cl. .......................................... 800/20; 800/3
(58) Field of Classification Search .................... 800/8, 800/20, 3
See application file for complete search history.

(56) References Cited

U.S. PATENT DOCUMENTS

2004/0093630 A1* 5/2004 Huh et al. .................... 800/20

OTHER PUBLICATIONS

Winkler et al. Genome Res. 13:1067-1081; 2003.*
Koster et al. Dev. Biol. 233:329-346; 2001.*
Chang et al BBRC 321:502-509; 2004.*
Airaksinen, M. S. and Saarma, M. (2002). The GDNF family: signalling, biological functions and therapeutic value. Nat. Rev. Neurosci. 3: 383-394.
Airaksinen, M., Titievsky, A. and Saarma, M. (1999). GDNF family neurotrophic factor signaling: four masters, one servant? Mol. Cell. Neurosci. 13: 313-325.
Arenas, E., Trupp, M., Åkerud, P. and Ibañéz, C. F. (1995). GDNF prevents degeneration and promotes the phenotype of brain noradrenergic neurons in vivo. Neuron 15: 1465-1473.
Chang, M. H., Huang, C. J., Lu, I. C., Kuo, T. F., and Chou, C. M. (2004) Zebrafish heparin-binding neurite promoting factor, HBNF, enhances neurite outgrowth during its development. Biochem. Biophys. Res. Commun. 321: 502-509.
Crowder, R. J. and Freeman, R. S. (1998) Phosphatidylinositol 3-kinase and Akt protein kinase are necessary and sufficient for the survival of nerve growth factordependent sympathetic neurons. J. Neurosci. 18: 2933-2943.
Feng, Y., Matsuura, N., and Ubukata, M. (2004) Indocarbazostatins C and D, new inhibitors of NGF-induced neuronal differentiation in PC12 cells. J. Antibiot. (Tokyo). 57:627-633.
Gill, S. S., Patel, N. K., Hotton, G. R., O'Sullivan, K., McCarter, R., Bunnage, M., Brooks, D. J., Svendesen, C. N. and Heywood, P.

(2003). Direct brain infusion of glial cell line-derived neurotrophic factor in Parkisnson disease. Nat. Med. 9: 589-595.
Gong, Z., Ju, B., Wan, H. (2001) Green fluorescent protein (GFP) transgenic fish and their applications. Genetica 111: 213-225.
Greene, L. A., Tischler, A. S. (1976) Establishment of a noradrenergic clonal line of rat adrenal pheochromocytoma cells which respond to nerve growth factor. Proc. Natl. Acad. Sci. U S A. 73: 2424-2428.
Hampton, B. S., Marshak, D. R., Burgess, W. H. (1992) Structural and functional characterization of full-length heparin-binding growth associated molecule. Mol. Biol. Cell 3: 85-93.
Henderson, C. E., Phillips, H. S., Pollock, R. A., Davies, A. M., Lemeulle, C., Armanini, M., Simmons, L., Moffet, B., Vandlen, R. A. and Rosenthal, A. (1994). GDNF: A potent survival factor for motoneurons present in peripheral nerve and muscle. Science 266: 1062-1064.
Her, G. M., Yeh, Y. H., Wu, J. L. (2003) 435-bp liver regulatory sequence in the liver fatty acid binding protein (L-FABP) gene is sufficient to modulate liver regional expression in transgenic zebrafish. Dev Dyn. 227: 347-356.
Her, G. M., Chiang, C. C., Wu, J. L. (2004) Zebrafish intestinal fatty acid binding protein (I-FABP) gene promoter drives gut-specific expression in stable transgenic fish. Genesis.38: 26-31.
Hiwasa, T., Kondo, K., Hishiki, T., Koshizawa, S., Umezawa, K., and Nakagawara, A. (1997) GDNF-induced neurite formation was stimulated by protein kinase inhibitors and suppressed by Ras inhibitors. Neurosci. Lett. 238: 115-118.
Kinnunen, T., Raulo, E., Nolo, R., Maccarana, M., Lindahl, U., Rauvala, H. (1996) Neurite outgrowth in brain neurons induced by heparin-binding growth-ssociated molecule (HB-GAM) depends on the specific interaction of HB-GAM with heparan sulfate at the cell surface. J. Biol. Chem. 271: 2243-2248.
Kuo, M. D., Oda, Y., Huang, J. S., Huang, S. S. (1990) Amino acid sequence and characterization of a heparin-binding neurite-promoting factor (p18) from bovine brain. J. Biol. Chem. 265: 18749-18752.
Lawson, N. D., Weinstein, B. M. (2002) In vivo imaging of embryonic vascular development using transgenic zebrafish. Dev Biol. 248: 307-318.
Li, Y., Chen, X., Satake, M., Oshima, Y., Ohizumi, Y. (2004) Acetylated flavonoid glycosides potentiating NGF action from *Scoparia dulcis*. J. Nat. Prod. 67: 725-727.
Li, Y. S., Milner, P. G., Chauhan, A. K., Watson, M. A., Hoffman, R. M., Kodner, C. M., Milbrandt, J., Deuel, T. F. (1990) Cloning and expression of a developmentally regulated protein that induces mitogenic and neurite outgrowth activity. Science 250: 1690-1694.
Li, Y. S., Deuel, T. F. (1993) Pleiotrophin stimulates tyrosine phosphorylation in NIH 3T3 and NB41A3 cells. Biochem. Biophys. Res. Commun. 195: 1089-1095.
Lin, L. F., Doherty, D. H., Lile, J. D., Bektesh, S., and Collins, F. (1993) GDNF: a glial cell line-derived neurotrophic factor for midbrain dopaminergic neurons. Science 260: 1130-1132.

(Continued)

*Primary Examiner*—Fereydoun G Sajjadi
(74) *Attorney, Agent, or Firm*—Hsiu-Ming Saunders; Intellectual Property Connections, Inc.

(57) ABSTRACT

A genetically modified zebrafish embryo, comprising a HBNF cDNA or a NGF cDNA or a GDNF cDNA together with a cDNA encoding green fluorescent protein (GFP) so as to induce neurite outgrowth during said zebrafish embryonic development, and a method of using such genetically modified zebrafish embryo to identify a therapeutic agent are disclosed.

12 Claims, 4 Drawing Sheets

OTHER PUBLICATIONS

Parng, C., Seng, W. L., Semino, C., McGrath, P. (2002) Zebrafish: a preclinical model for drug screening. Assay Drug Dev Technol. 1 (1 Pt 1): 41-48.

Raulo, E., Julkunen, I., Merenmies, J., Pihlaskari, R., Rauvala, H. (1992) Secretion and biological activities of heparin-binding growth-associated molecule: neurite outgrowth-promoting and mitogenic actions of the recombinant and tissue-derived protein. J. Biol. Chem. 267: 11408-11416.

Raulo, E., Chernousov, M. A., Carey, D. J., Nolo, R., Rauvala, H. (1994) Isolation of a neuronal cell surface receptor of heparin binding growth-associated molecule (HB-GAM). J. Biol. Chem. 269: 12999-13004.

Rauvala, H. (1989) An 18-kd heparin-binding protein of developing brain that is distinct from fibroblast growth factors. EMBO J. 8: 2933-2941.

Rauvala, H., Peng, H. B. (1997) HB-GAM (Hepairn-binding growth-associated molecule) and heparin-type glycans in the development and plasticity of neuron-target contacts. Prog. Neurobiol. 52: 127-144.

Rubinstein, A. L. (2003) Zebrafish: from disease modeling to drug discovery. Curr Opin Drug Discov Devel. 6: 218-223.

Sariola, H. and Saarma, M. (1999). GDNF and its receptor in the regulation of ureteric branching. Int. J. Dev. Biol. 43: 413-418.

Seddon, A. P., et al., Refolding and Characterization of Human /Recombinant Heparin-Binding Neurite-Promoting Factor, Protein Expression and Purification 5, 14-21 (1994).

Shafizadeh, E., Peterson, R., Lin, S., Induction of reversible hemolytic anemia in living zebrafish using a novel small molecule. Comp. Bio. and Phys., Part C 138 (2004) 245-249.

Shentu, H., Wen, H. J., Her, G. M., Huang, C. J., Wu, J. L., Hwang, S. P. (2003) Proximal upstream region of zebrafish bone morphogenetic protein 4 promoter directs heart expression of green fluorescent protein. Genesis. 37: 103-112.

Simpson, P. B., Bacha, J. I., Palfreyman, E. L., Woollacott, A. J., McKernan, R. M., Kerby, J. (2001) Retinoic acid evoked-differentiation of neuroblastoma cells predominates over growth factor stimulation: an automated image capture and quantitation approach to neuritogenesis. Anal. Biochem. 298: 163-169.

Urtishak, K. A., Choob, M., Tian, X., Sternheim, N., Talbot, W. S., Wickstrom, E., Farber, S. A. (2003) Targeted gene knockdown in zebrafish using negatively charged peptide nucleic acid mimics. Dev. Dyn. 228: 405-413.

Winkler, C., Schafer, M., Duschl, J., Schartl, M., Volff, J. N. (2003) Functional divergence of two zebrafish midkine growth factors following fish-specific gene duplication. Genome Res. 13: 1067-1081.

* cited by examiner

SEQUENCE LISTING

<160> NUMBER OF SEQ ID NOS: 2

<210> SEQ ID NO 1
<211> LENGTH: 158
<212> TYPE: PRT
<213> ORGANISM: Danio rerio

<400> SEQUENCE: 1

```
Met Gln Gln Gln Trp Val Cys Val Ala Leu Leu Ala Leu Leu Thr Val
1               5                   10                  15

Thr Ala Thr Leu Ala Asp Gly Gly Lys Thr Glu Lys Gln Gly Lys Lys
            20                  25                  30

Glu Arg Lys Ser Asp Cys Gly Glu Trp Gln Trp Ser Val Cys Val Ala
        35                  40                  45

Asn Glu Gly Asp Cys Gly Leu Gly Ile Arg Glu Gly Thr Arg Ser Gly
```

-continued

```
                50                  55                  60
Asn Asp Cys Lys Gln Thr Ile Lys Thr Gln Arg Cys Lys Ile Pro Cys
 65                  70                  75                  80

Asn Trp Lys Lys Gln Phe Gly Gly Glu Cys Lys Tyr Asp Phe Gln Ala
                 85                  90                  95

Trp Gly Glu Cys Asp Ser Thr Thr Gly Met Lys Thr Arg Thr Gly Val
                100                 105                 110

Leu Lys Arg Ala Leu Met Asp Ala Asn Cys Pro Asn Thr Val Ser Ala
                115                 120                 125

Thr Lys Pro Cys Gly Lys Pro Lys Thr Lys Met Gln Asp Ser Gln Lys
                130                 135                 140

Pro Lys Arg Asp Gly Lys Lys Lys Glu Arg Asn Pro Thr Asp
145                 150                 155
```

<210> SEQ ID NO 2
<211> LENGTH: 1023
<212> TYPE: DNA
<213> ORGANISM: Danio rerio

<400> SEQUENCE: 2

```
cacggctcta gtggatatag aaagctaggg ataaaaagag agaggaagca aaaggtgga      60
attaggaaca aaaccaaac tattcctcag actacagcat gcagcagcag tgggtgtgtg    120
tggctttatt agccctcctg actgtcacag caacacttgc agatggtggg aaaacagaaa    180
aacaaggtaa gaaagagcgt aaatcggact gtggagagtg gcagtggagt gtgtgtgtgg    240
ccaatgaggg cgactgcgga ttgggaatca gagagggcac acgctccggc aatgactgca    300
aacagaccat caaaacccag cgctgcaaaa tcccatgcaa ctggaagaag cagtttggag    360
gtgagtgtaa gtatgatttc caggcatggg gagagtgtga ttcgaccaca ggaatgaaga    420
ctcgcactgg agtgctaaag cgagcgctga tggatgctaa ctgtccaaac acagtcagcg    480
ccaccaaacc ctgtggcaaa cccaagacca agatgcaaga ctctcagaaa ccaaaacggg    540
acggaaagaa gaaggagcga aaccctacag actagaggag gaaaactcct gaagcgtctc    600
cttctgcctc ctgaagacgc ttcctattcc tcatgctata tttttagatc ttttgtagcg    660
ttcacttaca gctcacccag tactaaataa gagagaaaga gaaacgcaaa tgagtctact    720
aaaatcttca acacaaaaat ctgagatgac agaaagcaca actgaaagag tgttttattg    780
cattgatgag tgtgtgttta attggcctca tcaaacagtg tcttcgacta gagtgtgaag    840
cagaacttac tgagttttac attagtagag aattattact gttttaatgc agcatttggt    900
cattgattta tgcagcactg attattaaca tcatctgatg cttctcaaac atccctgcat    960
atttaacagt gaaataaaac aagtgtacta ttggaaaaaa aaaaaaaaaa aaaaaaaaa   1020
aaa                                                                1023
```

IN VIVO ASSAY FOR NEURITE OUTGROWTH IN ZEBRAFISH AND ITS APPLICATION IN DRUG SCREENING

RELATED APPLICATIONS

This application claims priority from U.S. Provisional Patent Application Ser. No. 60/642,064 which was filed on Jan. 7, 2005.

BACKGROUND OF THE INVENTION

1. Field of the Invention

The present invention relates to a novel in vivo system that can be used to screen or test therapeutic agents for treating neurodegenerative illnesses. Specifically, the in vivo system of the present invention is established by using zebrafish embryos coupled with following the neurite outgrowth from green fluorescent protein (GFP)—labeled neurons during zebrafish development.

2. Description of the Related Art

The assessment of neurite-promoting activity of growth factors and neurotrophins in vitro is usually done by the laborious process of counting neuronal processes manually under a standard microscope or confocal microscopy. But more recently, automated methods have become available. Automated monitoring and quantification of neurite formation and outgrowth in multiple samples have greatly enhanced therapeutic investigations in neuroscience, particularly in drug screening and the drug discovery process in general (Simpson et al., 2001). However, these methods still offer relatively low throughput in terms of detection when compared with other higher-throughput screens, and they are limited to targeted screens or purely secondary screens.

In neuroscience research, many projects are focused on identifying drugs that affect the growth of neurites. The discovery and characterization of compounds and new chemical entities that promote or suppress neuritogenesis are of great importance in the search for therapies to treat neurodegenerative illnesses, such as Alzheimer's disease and Parkinson's disease, as well as trauma that results in neuropathy and nerve injury, including stroke and spinal cord injuries (Makarovsky et al., 2003).

Heparin-binding Neurite-promoting Factor (HBNF)

Heparin-binding neurotrophic factor or neurite-promoting factor (HBNF) was first co-purified with bovine acidic fibroblast growth factor from brain tissues (Rauvala, 1989). It is a secretory heparin-binding protein with highly basic and cysteine-rich amino acid residues. In mammals, HBNF shares 50% identity with midkine (MK) and they constitute a new family of heparin-binding proteins (Kovesdi et al., 1990). HBNF and MK are not only functionally related proteins with similar promotion of neurite extension in PC12 cells (Kretschmer et al., 1991; Bohlen et al., 1991), but also structurally related proteins. They have two conserved cysteine residues, a highly conserved hinge region as well as two clusters of basic residues for heparin binding (Winkler et al., 2003). In addition to neurite outgrowth promotion, HBNF also has a variety of biological activities, such as stimulating cell growth, acting as an angiogenesis factor, and containing oncogenic activity. Therefore, it is also known as pleiotrophin (PTN) (Li et al., 1990) and heparin-binding growth-associated molecule (HB-GAM) (Merenmies et al., 1990).

Initially, the function of HBNF/PTN was found to promote neurite outgrowth from different cultured neuronal cell types, including primary embryonic cortical neurons (Hampton et al., 1992; Raulo et al., 1992), PC12 cells (Kuo et al., 1990) and neuroblastoma cells (Li et al., 1993). PC12 cells are derived from a transplantable rat pheochromocytoma with an important feature of responding to nerve growth factor (NGF) to differentiate into neuron-like cells. Upon exposure to NGF, PC12 cells cease proliferation and extend neuritis (Greene and Tischler, 1976). Without NGF, HBNF could induce weak but significant neurite extension in PC12 cells, when these cells were transfected with HBNF cDNA (Chang et al., 2004).

HBNF Receptor, syndecan-3, is a haparan sulfate proteoglycan

HBNF/PTN was first isolated as a heparin-binding protein with high affinity, suggesting that heparin or heparin-type carbohydrates may play important roles in the biological function of HBNF/PTN (Rauvala 1989). Indeed, further studies demonstrate that a transmembrane heparan sulfate proteoglycan, N-syndecan (syndecan-3), acts as a receptor for HBNF/PTN (Raulo et al., 1994). Both the heparan sulfate side chains of N-syndecan and polyclonal anti-N-syndecan inhibit HBNF/PTN-induced neurite outgrowth in the cultured neurons. In addition to N-syndecan heparan sulphate, the low molecular weight heparin displays more potent inhibition of HBNF/PTN-induced neurite outgrowth in cultured neuronal cells (Kinnunen et al., 1996; Rauvala et al., 1997). As mentioned above, we modified the in vivo neurite outgrowth assay in zebrafish embryos to investigate the inhibitory effect of heparin or heparan sulfate on HBNF-induced neurite outgrowth by further injection of different dosage of heparin or heparan sulfate into zebrafish embryo at two- or four-cell stage. In agreement with previous report (Rauvala et al., 1997), heparin could inhibit HBNF-induced neurite outgrowth in zebrafish embryos (data not shown). Therefore, the modified assay system also can be used to compare the inhibitory or enhancing effect of HBNF/PTN-induced neurite outgrowth in vivo by heparin and its modified forms, N-syndecan-derived saccharides, and other glycosaminoglycans.

Compounds with Enhancing or Inhibitory Effect on NGF-induced Neurite Outgrowth in PC12 Cells

*Scoparia dulcis* L. (Scrophulariaceae) is a widespread tropical herbaceous medicinal plant, which has been used widely as a traditional folk medicine for its antipyretic and analgesic properties and for its use in treating bronchitis and gastric disorders in South America. Three new acetylated flavonoid glycosides, 5,6,4'-trihydroxyflavone 7-O-alpha-L-2,3-di-O-acetylrhamnopyranosyl-(1→6)-beta-D-glucopyranoside (1), apigenin 7-O-alpha-L-3-O-acetylrhamnopyranosyl-(1→6)-beta-D-glucopyranoside (2), and apigenin 7-O-alpha-L-2,3-di-O-acetylrhamnopyranosyl-(1→6)-beta-D-glucopyranoside (3), were isolated from *Scoparia dulcis* together with the known compound eugenyl beta-D-glucopyranoside (4). Compounds 2 and 3 showed an enhancing activity of nerve growth factor-mediated neurite outgrowth in PC12D cells (Li et al., 2004).

Indocarbazostatins C (3) and D (4), new inhibitors of NGF-induced neurite outgrowth were isolated from culture broth of a mutant strain, Streptomyces sp. MUV-6-83 (Feng et al., 2004). The structural elucidation of 3 and 4 revealed that these inhibitors were methyl ester analogs of the corresponding ethyl ester compounds, indocarbazostatin (1) and indocarbazostatin B (2), respectively.

Zebrafish

Zebrafish is a good model organism for the study of vertebrate development (Penberthy et al., 2002; Rubinstein, 2003). The embryos develop outside the mother and are optically transparent, allowing direct observation of their embryonic development that takes only 48 hours for completion at 28° C. In my lab, we have cloned several zebrafish tissue-specific promoters including pancreatic-, neuron-, and muscle-specific promoters. Their tissue specificies of gene expression were confirmed by expression of GFP in zebrafish embryos. Therefore, these tissue-specific promoters could be used to drive GFP or RFP expression in zebrafish embryos. In general, it is common to investigate the function of known or novel genes by gain-of-function and loss-of-function in zebrafish. To achieve gain-of-function, genes of interest are driven by tissue-specific promoters and injected into one-cell zebrafish embryos (Gong et al., 2001). Alternatively, the expression constructs under the control of either ubiquitous or tissue-specific promoter were co-injected with tissue-specific promoter/GFP construct. On the other hand, to achieve loss-of-function, genes of interest are knockdowned by injection of morpholino antisense-oligomnucleotides (MAO) or coinjection of MAO with tissue-specific promoter/GFP construct (Nasevicius and Ekker, 2000; Urtishak et al., 2003). The suitable transgenic GFP/RFP zebrafishes also can be used to inject MAO or expression constructs, respectively.

Recently, many transgenic zebrafish with fluorescent organs for development of relevant models of human disease have been established (Shentu et al., 2003; Her et al., 2003; Her, et al., 2004). For example, transgenic lines of zebrafish with fluorescent blood vessels have been developed, which simplifies the process by which blood vessels are visualized (Lawson and Weinstein, 2002). This transgenic line was designed by driving expression of green fluorescent protein (GFP) with the fli-1promoter. Embryos and larvae with fluorescent blood vessels can be used for angiogenesis assays. The VEGF-specific tyrosine kinase inhibitor SU-5416 (semaxanib; SUGEN Inc) and the more broadly active tyrosine kinase inhibitor, SU-6668 (SUGEN Inc) have been found to inhibit angiogenesis in transgenic fluorescent embryos (Parng et al., 2002).

Enhancement of Neurite Outgrowth in Zebrafish Embryo

So far, there is no suitable in vivo assay to assess the enhancement of neurite outgrowth by neurite-promoting factors. In our lab, we used zebrafish embryos to establish an in vivo system that can be used to study the enhancement of neurite outgrowth from GFP-labeled live neurons during zebrafish development (Chang et al., 2004). Zebrafish embryos could provide more additional factors than those in PC12 cells for extensive neurite outgrowth. In zebrafish, HuC gene has been shown to be a useful early marker for neurons and a 2.8 kb promoter region of this gene is sufficient to direct GFP expression in a neuron-specific pattern closely similar to endogenous HuC expression (Park et al., 2000). As shown in the following data, pHuC-GFP alone displayed GFP expression in trigeminal gaglion, axon as well as rohon beard (RB) or motor neurons without visible branched and long neurites. However, coinjection of pcDNA-HBNF-HA and pHuC-GFP resulted in significant enhancement of neurite outgrowth with extensive branched and long dendrites. For the first time, these data indicated that the expression of zebrafish HBNF could induce robust neurite outgrowth with wider and complicate branches from GFP-labeled neurons during zebrafish development.

SUMMARY OF THE INVENTION

An object of the present invention is to develop a genetically modified zebrafish embryo, comprising a cDNA encoding heparin-binding neurotrophic factor (HBNF), or a cDNA encoding nerve growth factor (NGF), or a cDNA encoding glial-derived neurotrophic factor (GDNF) together with a cDNA encoding green fluorescent protein (GFP) so as to induce neurite outgrowth during said zebrafish embryonic development.

Another object of the present invention is to develop a method of identifying a therapeutic agent that affects the growth of neurites, comprising the steps of:

a) introducing a GFP cDNA into a zebrafish embryo at one-cell or two-cell stage to form a genetically modified zebrafish embryo;

b) incubating said genetically modified zebrafish embryo in a medium suitable for the growth of said transgenic zebrafish embryo for about six hours;

c) adding said therapeutic agent into said medium containing said genetically modified zebrafish embryo; and d) counting neurite outgrowth in said genetically modified zebrafish embryo at about 24, 48 and 72 hours after adding said therapeutic agent.

Another object of the present invention is to develop a method of identifying a therapeutic agent that affects the growth of neurites, comprising the steps of:

a) co-introducing a GFP cDNA together with a HBNF cDNA or a NGF cDNA or a GDNF cDNA into a zebrafish embryo at one-cell or two-cell stage to form a genetically modified zebrafish embryo;

b) incubating said transgenic zebrafish embryo in a medium suitable for the growth of said genetically modified zebrafish embryo for about six hours;

c) adding said therapeutic agent into said medium containing said genetically modified zebrafish embryo; and d) counting neurite outgrowth in said genetically modified zebrafish embryo at about 24, 48 and 72 hours after adding said therapeutic agent.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

PC12 cells were transfected with one microgram of pHA-YUN (A) or pcDNA-HBNF-HA (B). After 72 h posttransfection, cells were observed under inverted microscope. Images of cell morphology were taken by using the SPOT system. Bars, 10 um.

Figure 2:
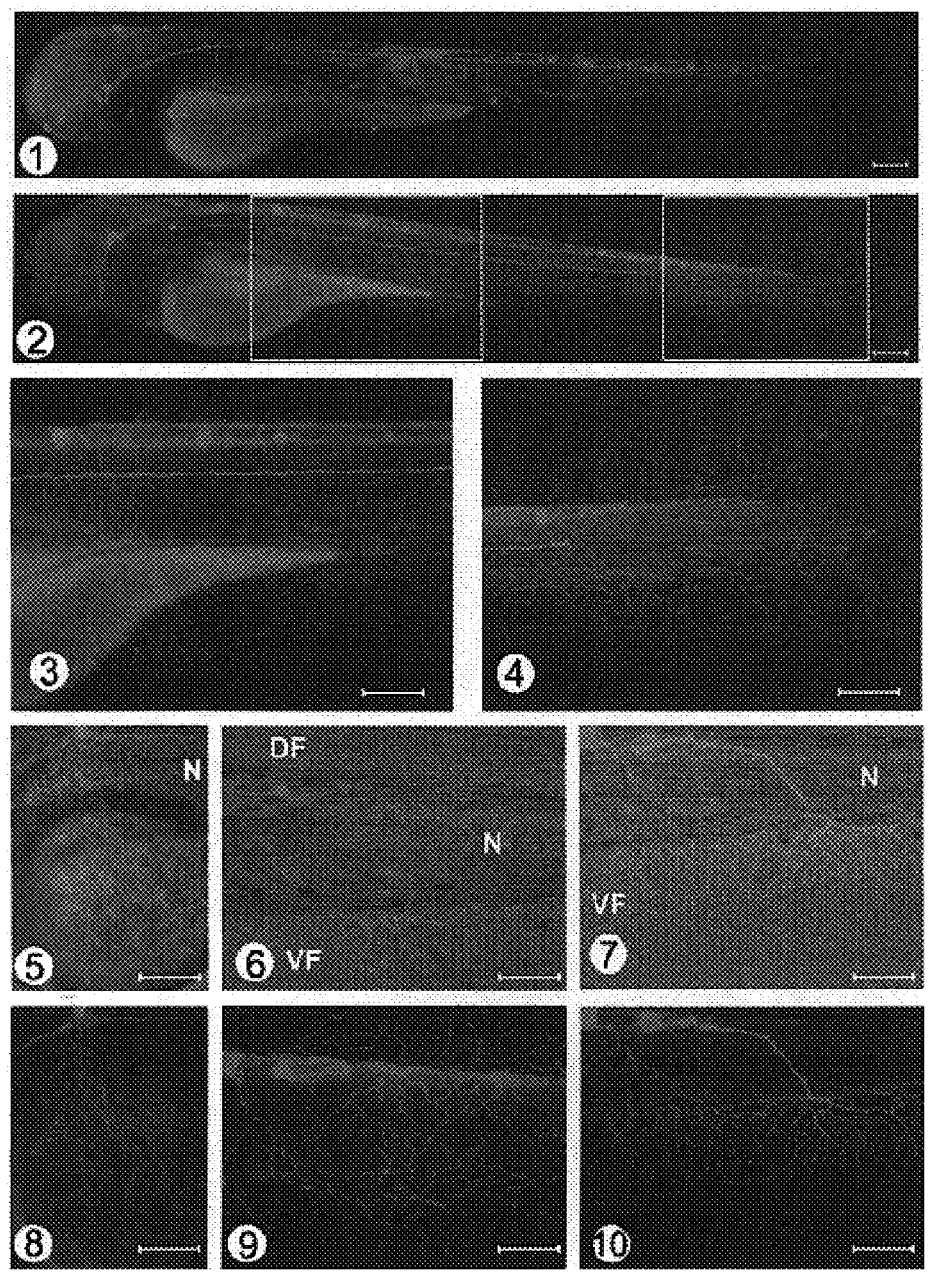

FIG. 2. Enhancement of neurite outgrowth by HBNF protein in zebrafish embryos.

The expression construct pcDNA-HBNF-HA and pHuC-GFP (panels 2, 5-7) were coinjected into zebrafish embryos at 1-cell stage. Similar injection of pHuC-GFP alone (panel 1) was used as control. Zebrafish embryos at 72 h postfertilization with GFP fluorescence were selected for image analysis. Embryos are shown as lateral view with anterior to the left. Experiments were repeated at least three times and at least 100 fertilized eggs were used for injection of expression constructs at each time. Four representative patterns with significant enhancement of neurite outgrowth (panels 2, 5-7) were shown. Images of bright field and fluorescence were merged and shown in panels 1, 2, and 5-7, while fluorescence images only in panels 3, 4, 8-10. Higher magnification of two regions marked with yellow boxes in panel 2 was shown in panel 3 and 4, respectively. N, notochord; DF, dorsal fin; VF, ventral fin. Scale bars represent 100 µm.

Figure 3:
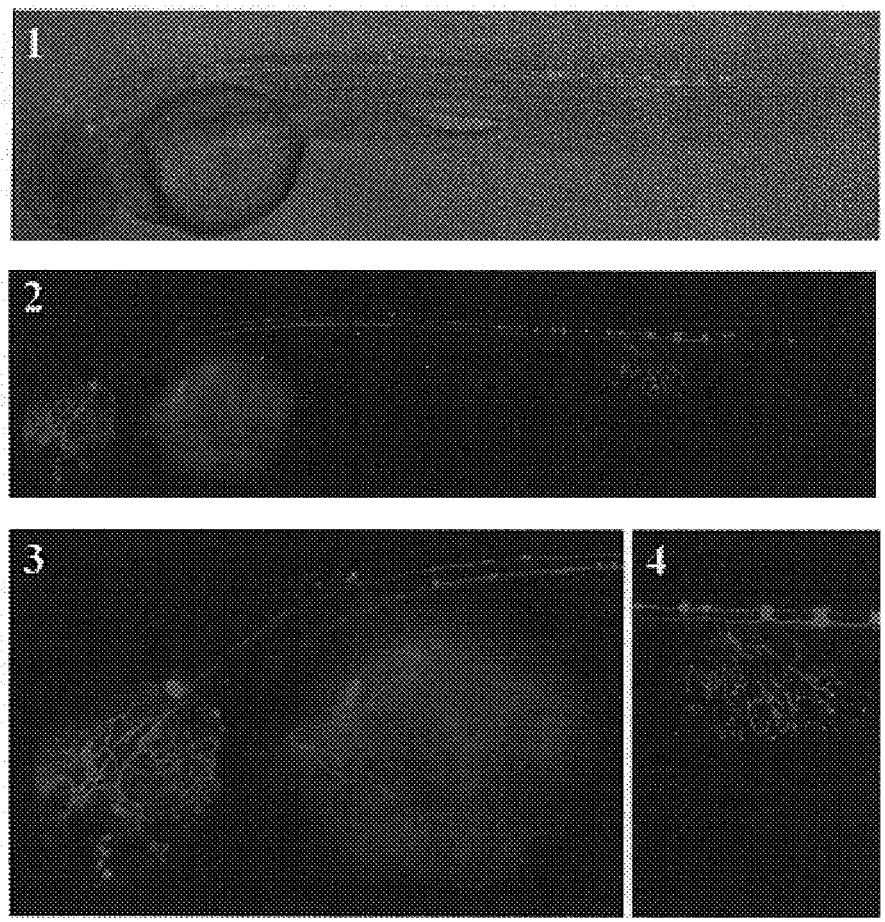

FIG. 3. Enhancement of neurite outgrowth by NGF in zebrafish embryos.

The expression construct pcDNA-NGF-HA and pHuC-GFP were coinjected into zebrafish embryos at 1-cell stage. Similar injection of pHuC-GFP alone was used as control. Zebrafish embryos at 72 hpf with GFP fluorescence were selected for image analysis. Embryos are shown as lateral view with anterior to the left. Images of bright field and fluorescence were merged and shown in panel 1, while fluorescence images only in panel 2. Higher magnification of the head region and tail region with significant neurite outgrowth in panel 2 was shown in panels 3 and 4, respectively.

Figure 4:
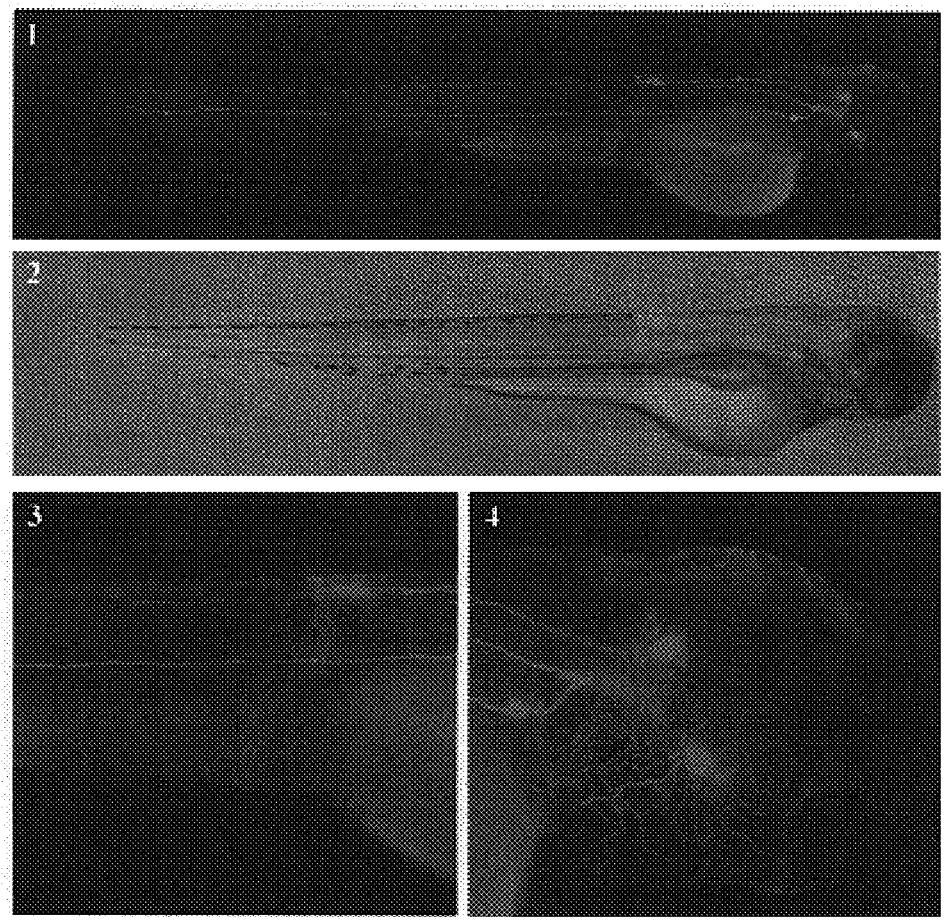

FIG. 4. Enhancement of neurite outgrowth by GDNF in zebrafish embryos.

The expression construct pGFAP-GDNF-HA and pHuC-GFP were coinjected into zebrafish embryos at 1-cell stage. Similar injection of pHuC-GFP alone was used as control. Zebrafish embryos at 48 hpf with GFP fluorescence were selected for image analysis. Embryos are shown as lateral view with anterior to the right. Images of bright field and fluorescence were merged and shown in panel 1, while fluorescence images only in panel 2. Higher magnification of the head region and trunk region with significant neurite outgrowth in panel 2 was shown in panels 3 and 4, respectively.

DETAILED DESCRIPTION OF THE PRESENTLY PREFERRED EMBODIMENTS

HBNF-induced Neurite Outgrowth in Zebrafish (Chang et al., 2004)

Figure 1:
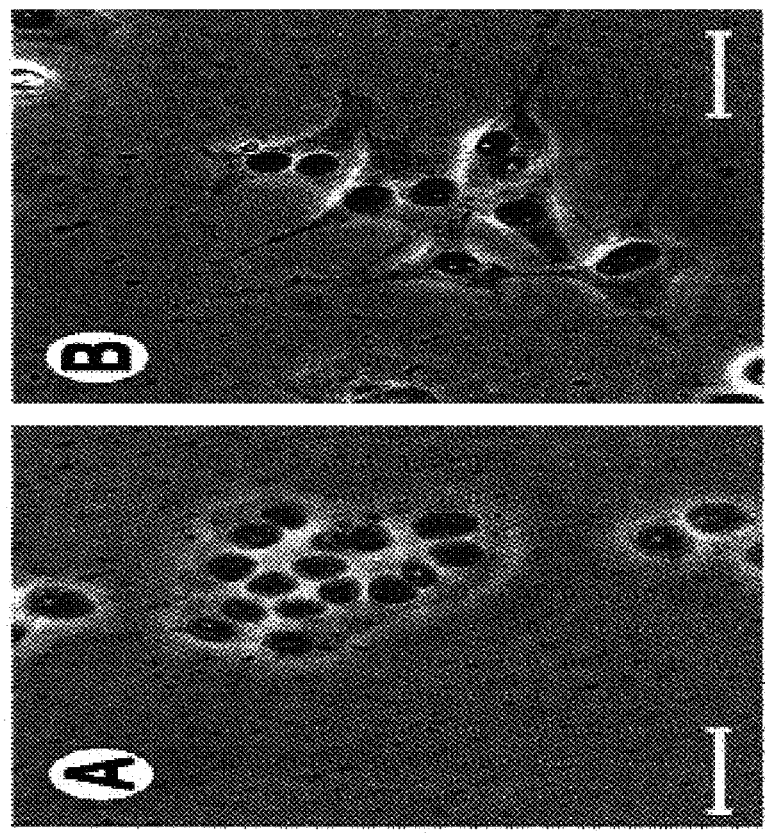
FIG. 1. Zebrafish HBNF induces neurite outgrowth in PC12 cells.

Heparin-binding neurotrophic factor, HBNF, is a secreted heparin-binding protein containing highly basic and cysteine-rich amino acid residues. We have cloned the full-length HBNF cDNA from zebrafish. The overall amino acid sequence of zebrafish HBNF shows 60% identity to human HBNF, but with approximately 40% identity to other midkine proteins. Like mammalian homolog, zebrafish HBNF could induce significant neurite outgrowth in PC12 cells without NGF stimulation (FIG. 1). In addition, zebrafish HBNF was able to enhance extensive neurite outgrowth in zebrafish embryos observed by an in vivo neurite outgrowth promotion assay. In this assay, we used the GFP gene as the reporter gene driven by a neuron-specific promoter, HuC promoter (Park et al., 2000). The expression construct of pcDNA-HBNF-HA was coinjected with pHuC-GFP into zebrafish embryos at one-cell stage. Several expression patterns with strong enhancement of neurite outgrowth in this assay were shown in FIG. 2. It is interesting to note that pHuC-GFP alone displayed stronger GFP expression in trigeminal gaglion, axon as well as interneurons (panel 1). However, coinjection of pcDNA-HBNF-HA and pHuC-GFP not only showed similar GFP expression pattern as that of pHuC-GFP alone, but also displayed significant enhancement of neurite outgrowth (panels 2-4). Other zebrafishes with neurite outgrowth enhancement were also presented, but with different branching patterns (panels 5-10). In addition, we generated another expression construct pCMV-HBNF-HuC-GFP containing two promoters and two genes and this construct displayed similar expression pattern as that of coinjection of pcDNA-HBNF-HA and pHuC-GFP (data not shown).

NGF-induced Neurite Outgrowth in Zebrafish

Nerve growth factor (NGF) is the prototypical member of the neurotrophin family, which has multiple effects on susceptible precursor and mature neuronal populations, including antiapoptosis, differentiation, phenotypic maintenance, and regeneration (Barde, 1989). Binding of NGF to its receptor, TrkA, activates the PI3K signaling pathway, leading to activation of Akt in sympathetic neurons (Crowder and Freeman, 1998). Engagement of TrkA by NGF also leads to activation of Erk1/2 (Liu et al. 2003). Like mammalian homolog, zebrafish NGF was able to induce extensive neurite outgrowth in zebrafish embryos. The expression construct of pCMV-NGF-HA was coinjected with pHuC-GFP into zebrafish embryos at one-cell stage. Like the effect of HBNF, zebrafish NGF could induce strong enhancement of neurite outgrowth in this assay as shown in FIG. 3. In addition, we generated another expression construct pCMV-NGF-HuC-GFP containing two promoters and two genes and this construct displayed similar expression pattern as that of coinjection of pCMV-NGF-HA and pHuC-GFP.

GDNF-induced Neurite Outgrowth in Zebrafish

Glial-derived neurotrophic factor (GDNF) was first purified and characterized as a growth factor promoting the survival of the embryonic dopaminergic neurons of the midbrain, i.e. those neurons that degenerate in Parkinson disease (Lin et al., 1993). Subsequently, it was shown that GDNF is also a very potent trophic factor for spinal motoneurons (Henderson et al., 1994) and central noradrenergic neurons (Arenas et al., 1995). A recent clinical trial indicates that, when the GDNF is infused directly in putamen, it is an effective treatment for Parkinson disease and does not have significant side-effects (Gill et al., 2003). GDNF is a member of the GDNF family ligands (GFLs) and supports the survival of central, peripheral, and autonomic neuron populations (Airaksinen et al., 1999). A common receptor, RET, modulates the action of this family and a co-receptor, GFRalpha, determines RET ligand specificity (Airaksinen and Saarma, 2002). From animal studies, GDNF appears to be essential for enteric nervous system (ENS) development in mammals (Sariola and Saarma, 1999). However, the recombinant GDNF could induce neurite outgrowth of neuro2A neuroblastoma cells (Hiwasa et al., 1997). Like mammalian homolog, zebrafish GDNF was able to induce extensive neurite outgrowth in zebrafish embryos. The expression construct of pGFAP-GDNF-HA was coinjected with pHuC-GFP into zebrafish embryos at one-cell stage. Like the effect of HBNF and NGF, glia cells-produced GDNF could induce enhancement of neurite outgrowth in this assay as shown in FIG. 4. In addition, we generated another expression construct pGFAP-GDNF-HuC-GFP containing two promoters and two genes and this construct displayed similar expression pattern as that of coinjection of pGFAP-GDNF-HA and pHuC-GFP (data not shown).

Drug Screen for Promotion or Inhibition of Neurite Outgrowth in Zebrafish Embryos In neuroscience research, many projects are focused on identifying drugs that affect the growth of neurites. The discovery and characterization of compounds and new chemical entities that promote or suppress neuritogenesis are of great importance in the search for therapies to treat neurodegenerative illnesses, such as Alzheimer's disease and Parkinson's disease, as well as trauma that results in neuropathy and nerve injury, including stroke and spinal cord injuries (Makarovsky et al., 2003).

For screening the drug with the potential for promotion of neurite outgrowth in zebrafish embryos, we first injected pHuC-GFP into zebrafish embryos at one or two-cell stage and immersed the drug with different dilution in 96-well containing 3 injected embryos in each well at 6 h after injection. If the drug is not water soluble, it can be dissolved in DMSO to a final concentration between 10-100 mM. Then, each drug will be 10-fold diluted in DMSO. A minimal volume, 3 ul, of DMSO can be added to 300 ul fish water per well containing 3 embryos. The promotion of neurite outgrowth by drugs will be observed and counted at 24, 48 and 72 hpf. As described above, the activation of HBNF, NGF, or GDNF, respectively, can induce neurtire outgrowth. Therefore, if one drug can promote neurite outgrowth, we will further confirm such promotion of neurite outgrowth is activated through which pathway. The antagonist of the drug will be added to expression plasmid-injected embryos at 6 hpf to test whether it can inhibit the neurite outgrowth by HBNF, NGF, or GDNF, respectively.

Similarly, for screening the drug with the potential to inhibit neurite outgrowth in zebrafish embryos, we first injected pCMV-HBNF-HuC-GFP, pCMV-NGF-HuC-GFP, or pGFAP-GDNF-HuC-GFP, respectively, into zebrafish embryos at one or two-cell stage and immersed the drug with different dilution in 96-well containing 3 injected embryos in each well at 6 h after injection. The inhibition of neurite outgrowth by drug will be observed and counted at 24, 48 and 72 hpf.

In summary, we used zebrafish embryos to establish an in vivo assay system that can be used to screen drugs with the potential for the enhancement or inhibition of neurite outgrowth from GFP-labeled live neurons during zebrafish development.

The following examples further describe and explain the present invention, and are not limitations to the scope of the present invention.

EXAMPLE 1

Cell Cultures

Rat pheochromocytoma PC12 cells were cultured in Dulbecco's modified Eagle's medium (DMEM), supplemented with 10% fetal bovine serum (FBS, HyClone Co., Utah), penicillin G (50 units/ml), streptomycin (50 µg/ml), and L-glutamine (2 mM) in a humidified atmosphere of 5% $CO_2$ at 37° C. Various culture reagents used were purchased from HyClone Co. (Logan, Utah).

EXAMPLE 2

Fish

Zebrafish (*Danio rerio*) were maintained at 28° C. on a 14 h-light/10 h-dark cycle. Embryos were incubated at 28° C. and different developmental stages were determined according to the description in Zebrafish Book (Westerfield, 1995).

EXAMPLE 3

Isolation of Neuron-specific HuC and Glia-specific GFAP Promoter Regions

The zebrafish genomic DNA was prepared according to our previous report (Hsieh et al., 2003). The expected 3.5-kb promoter region of zebrafish Hu-C gene (Park et al., 2000; accession no AF173984) and 5-kb promoter region of zebrafish GFAP gene (accession no BX324157, nt 201833-206834) were obtained by PCR amplification and cloned into pGEM-T. Those sequences have been confirmed by DNA sequence analysis. Then, the promoter region was ligated to a promoter-less GFP reporter gene, pEGFP, (Clonetech) to generate the GFP reporter construct, such as pHuC-GFP or pGFAP-GFP.

EXAMPLE 4

Construction of Expression Plasmid and Cell Transfection

The expression plasmid, pcDNA-HBNF-HA (also called pCMV-HBNF-HA), was constructed by inserting the full-length zHBNF cDNA (accession no AY572239; SEQ ID NO: 2) into pcDNA3-HA at the BamHI and EcoRI sites, which allows the generation of the HBNF protein with in-framed HA tag at the C-terminal. The pcDNA3-HA plasmid was derived from pcDNA3 plasmid by adding the influenza A virus haemagglutinin (HA) tag (YPYDVPDYA) into pcDNA3 at the EcoRI and XhoI sites. The pHuC-GFP plasmid contains the GEP gene as the reporter gene and is driven by a zebrafish neuron-specific HuC promoter (Park et al., 2000). To investigate whether zebrafish HBNF (SEQ ID NO: 1) could induce neurite outgrowth in vitro, the full-length HBNF cDNA (SEQ ID NO: 2) under the control of CMV promoter was transiently transfected into PC12 cells. PC12 cells at 80% confluence were grown in a 6-wells dish and transiently transfected for 6 h at 37.degree. C. with 1 ug of pcDNA-HBNF-HA by using the Lipofectamin Kit (Life Technologies, MA). After 48 or 72 h cells were observed under an Olympus IX70-FLA inverted fluorescence microscope. Images were taken by using the SPOT system (Diagnostic Instruments, Inc., Sterling Heights, Mich.) and assembled by PhotoShop program (Adobe System Inc, California). In addition, serum-free supernatants of PC12 cells transfected with pcDNA-HBNF-HA were collected at 72 h after transfection.

Similarly, The expression plasmid, pcDNA-NGF-HA (also called pCMV-NGF-HA), was constructed by inserting the full-length zNGF cDNA (accession no NM_199210) into pcDNA3-HA at the BamHI and EcoRI sites. On the other hand, the expression plasmid, pGFAP-GDNF-HA, was constructed by inserting the full-length zGDNF cDNA (accession no NM_131595) into pGFAP-GFP at the BamHI and EcoRI sites.

To construct the chimeric plasmid containing two promoters and two genes, such as pCMV-HBNF-HuC-GFP, pCMV-NGF-HuC-GFP and pGFAP-GDNF-HuC-GFP, two different pairs of primers with Cla I sites on both ends were synthesized and used to amplify the DNA fragment containing CMV promoter and HBNF-HA or NGF-HA coding region as well as GFAP promoter and GDNF-HA coding region. The PCR products were cleaved by Cla I and cloned into the corresponding Cla I site in pHuC-GFP.

EXAMPLE 5

Western Blot Analysis

Monoclonal antibody against HA tag was purchased from Santa Cruze Biotechnology, Inc. (Santa Cruz, Calif.). Immunoblot analyses were performed by separating the supernatants of PC12 cells transfected with pcDNA-HBNF-HA on 10% SDS PAGE, followed by transferring to a PVDF membrane (Schleicher & Schuell, Dassel, Germany). The membranes were blocked with 4% skim milk in PBS and then incubated with anti-HA monoclonal antibody (1:3000 dilution) or anti-GFP polyclonal antibody (1:3000 dilution) at 4° C., overnight. After washing with PBST (0.2% Tween-20 in PBS) for three times, the membranes were incubated with horseradish peroxidase-conjugated sheep anti-mouse IgG antibody (1:5000, Amersham Biosciences Corp. Piscataway, N.J.) at room temperature for 2 h. The membranes were washed as described as above, and signals were detected using enhanced chemiluminescence (ECL) (NEN Life Science Products, Inc., Boston, Mass.).

EXAMPLE 6

Microinjection of Expression Plasmid into Zebrafish Embryos

The expression constructs, pcDNA-HBNF-HA (also called pCMV-HBNF-HA), pcDNA-NGF-HA (also called pCMV-NGF-HA), pGFAP-BDNF-HA and pHuC-GFP, were linearized by digestion with restriction enzyme ScaI, purified with PCR clean up/Gel extraction kit (Qiagen, BmbH, Germany). DNA concentration was adjusted to 100 ug/ml in 0.1 M KCl solution containing 0.5% phenol red and 100-200 pl of pHuC-GFP alone or in combination with pcDNA-HBNF-HA, pcDNA-NGF-HA or pGFAP-BDNF-HA, respectively, was microinjected into the zebrafish embryo at one-cell stage by using Narishige IM 300 microinjector system (Narishigi Scientitific Instrument Lab., Tokyo, Japan). Embryos at 48 h and 72 h postfertilization were observed under an Olympus IX70-FLA inverted fluorescence microscope. Images were taken by using the SPOT system and assembled by PhotoShop program.

It is apparent to a person of ordinary skill in the art that the references below cited throughout the present application are incorporated by reference in their entirety.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

REFERENCES

Airaksinen, M. S. and Saarma, M. (2002). The GDNF family: signalling, biological functions and therapeutic value. Nat. Rev. Neurosci. 3: 383-394.

Airaksinen, M., Titievsky, A. and Saarma, M. (1999). GDNF family neurotrophic factor signaling: four masters, one servant? Mol. Cell. Neurosci. 13: 313-325.

Arenas, E., Trupp, M., Åkerud, P. and Ibañéz, C. F. (1995). GDNF prevents degeneration and promotes the phenotype of brain noradrenergic neurons in vivo. Neuron 15: 1465-1473.

Barde, Y. A. (1989) Trophic factors and neuronal survival. Neuron 2: 1525-1534.

Bohlen, P., Muller, T., Gaustschi-Sova, P., Albrecht, U., Rasool, G. G., Decker, M., Seddon, A., Fafeur, V., Kovesdi, I., Kretschmer, P. J. (1991) Isolation from bovine brain and structural characterization of HBNF, heparin-binding neurotrophic factor. Growth Factors 4: 97-107.

Chang, M. H., Huang, C. J., Lu, I. C., Kuo, T. F., and Chou, C. M. (2004) Zebrafish heparin-binding neurite promoting factor, HBNF, enhances neurite outgrowth during its development. Biochem. Biophys. Res. Commun. 321: 502-509.

Crowder, R. J. and Freeman, R. S. (1998) Phosphatidylinositol 3-kinase and Akt protein kinase are necessary and sufficient for the survival of nerve growth factordependent sympathetic neurons. J. Neurosci. 18: 2933-2943.

Feng, Y., Matsuura, N., and Ubukata, M. (2004) Indocarbazostatins C and D, new inhibitors of NGF-induced neuronal differentiation in PC12 cells. J. Antibiot. (Tokyo). 57: 627-633.

Gill, S. S., Patel, N. K., Hotton, G. R., O'Sullivan, K., McCarter, R., Bunnage, M., Brooks, D. J., Svendesen, C. N. and Heywood, P. (2003). Direct brain infusion of glial cell line-derived neurotrophic factor in Parkisnson disease. Nat. Med. 9: 589-595.

Gong, Z., Ju, B., Wan, H. (2001) Green fluorescent protein (GFP) transgenic fish and their applications. Genetica 111: 213-225.

Greene, L. A., Tischler, A. S. (1976) Establishment of a noradrenergic clonal line of rat adrenal pheochromocytoma cells which respond to nerve growth factor. Proc. Natl. Acad. Sci. USA. 73: 2424-2428.

Hampton, B. S., Marshak, D. R., Burgess, W. H. (1992) Structural and functional characterization of full-length heparin-binding growth associated molecule. Mol. Biol. Cell 3: 85-93.

Henderson, C. E., Phillips, H. S., Pollock, R. A., Davies, A. M., Lemeulle, C., Armanini, M., Simmons, L., Moffet, B., Vandlen, R. A. and Rosenthal, A. (1994). GDNF: A potent survival factor for motoneurons present in peripheral nerve and muscle. Science 266: 1062-1064.

Her, G. M., Yeh, Y. H., Wu, J. L. (2003) 435-bp liver regulatory sequence in the liver fatty acid binding protein (L-FABP) gene is sufficient to modulate liver regional expression in transgenic zebrafish. Dev Dyn. 227: 347-356.

Her, G. M., Chiang, C. C., Wu, J. L. (2004) Zebrafish intestinal fatty acid binding protein (I-FABP) gene promoter drives gut-specific expression in stable transgenic fish. Genesis. 38: 26-31.

Hiwasa, T., Kondo, K., Hishiki, T., Koshizawa, S., Umezawa, K., and Nakagawara, A. (1997) GDNF-induced neurite formation was stimulated by protein kinase inhibitors and suppressed by Ras inhibitors. Neurosci. Lett. 238: 115-118.

Kinnunen, T., Raulo, E., Nolo, R., Maccarana, M., Lindahl, U., Rauvala, H. (1996) Neurite outgrowth in brain neurons induced by heparin-binding growth-associated molecule (HB-GAM) depends on the specific interaction of HB-GAM with heparan sulfate at the cell surface. J. Biol. Chem. 271: 2243-2248.

Kovesdi, I., Fairhurst, J. L., Kretschmer, P. J., Bohlen, P. (1990) Heparin-binding neurotrophic factor (HBNF) and MK, members of a new family of homologous, developmentally regulated proteins, Biochem. Biophys. Res. Commun. 172: 850-854.

Kretschmer, P. J., Fairhurst, J. L., Decker, M. M., Chan, C. P., Gluzman, Y., Bohlen, P., Kovesdi, I. (1991) Cloning, characterization and developmental regulation of two members of a novel human gene family of neurite outgrowth-promoting proteins. Growth Factors 5: 99-114.

Kuo, M. D., Oda, Y., Huang, J. S., Huang, S. S. (1990) Amino acid sequence and characterization of a heparin-binding neurite-promoting factor (p18) from bovine brain. J. Biol. Chem. 265: 18749-18752.

Lawson, N. D., Weinstein, B. M. (2002) In vivo imaging of embryonic vascular development using transgenic zebrafish. Dev Biol. 248: 307-318.

Li, Y., Chen, X., Satake, M., Oshima, Y., Ohizumi, Y. (2004) Acetylated flavonoid glycosides potentiating NGF action from Scoparia dulcis. J. Nat. Prod. 67: 725-727.

Li, Y. S., Milner, P. G., Chauhan, A. K., Watson, M. A., Hoffman, R. M., Kodner, C. M., Milbrandt, J., Deuel, T. F. (1990) Cloning and expression of a developmentally regulated protein that induces mitogenic and neurite outgrowth activity. Science 250: 1690-1694.

Li, Y. S., Deuel, T. F. (1993) Pleiotrophin stimulates tyrosine phosphorylation in NIH 3T3 and NB41A3 cells. Biochem. Biophys. Res. Commun. 195: 1089-1095.

Lin, L. F., Doherty, D. H., Lile, J. D., Bektesh, S., and Collins, F. (1993) GDNF: a glial cell line-derived neurotrophic factor for midbrain dopaminergic neurons. Science 260: 1130-1132.

Liu, H., Nowak, R., Chao, W., and Bloch, K. D. (2003) Nerve growth factor induces anti-apoptotic heme oxygenase-1 in rat pheochromocytoma PC-12 cells. J. Neurochem. 86: 1553-1563.

Makarovsky, D., Kalechman, Y., Sonino, T., Freidkin, I., Teitz, S., Albeck, M., Weil, M., Geffen-Aricha, R., Yadid, G., Sredni, B. (2003) Tellurium compound AS101 induces PC12 differentiation and rescues the neurons from apoptotic death. Ann NY Acad Sci. 1010: 659-666.

Merenmies, J., Rauvala, H. (1990) Molecular cloning of the 18-kDa growth-associated protein of developing brain. J. Biol. Chem. 265:16721-16724.

Nasevicius, A., and Ekker, S. C. (2000) Effective targeted gene 'knockdown' in zebrafish. Nat. Genet. 26: 216-220.

Park, H. C., Kim, C. H., Bae, Y. K., Yeo, S. Y., Kim, S. H., Hong, S. K., Shin, J., Yoo, K. W., Hibi, M., Hirano, T., Miki, N., Chitnis, A. B., Huh, T. L. (2000) Analysis of Upstream Elements in the HuC Promoter Leads to the Establishment of Transgenic Zebrafish with Fluorescent Neurons. Dev. Biol. 227: 279-293.

Parng, C., Seng, W. L., Semino, C., McGrath, P. (2002) Zebrafish: a preclinical model for drug screening. Assay Drug Dev Technol. 1 (1 Pt 1): 41-48.

Penberthy, W. T., Shafizadeh, E., Lin, S. (2002) The zebrafish as a model for human disease. Front Biosci. 7: d1439-d1453.

Raulo, E., Julkunen, I., Merenmies, J., Pihlaskari, R., Rauvala, H. (1992) Secretion and biological activities of heparin-binding growth-associated molecule: neurite outgrowth-promoting and mitogenic actions of the recombinant and tissue-derived protein. J. Biol. Chem. 267: 11408-11416.

Raulo, E., Chernousov, M. A., Carey, D. J., Nolo, R., Rauvala, H. (1994) Isolation of a neuronal cell surface receptor of heparin binding growth-associated molecule (HB-GAM). J. Biol. Chem. 269: 12999-13004.

Rauvala, H. (1989) An 18-kd heparin-binding protein of developing brain that is distinct from fibroblast growth factors. EMBO J. 8: 2933-2941.

Rauvala, H., Peng, H. B. (1997) HB-GAM (Hepairn-binding growth-associated molecule) and heparin-type glycans in the development and plasticity of neuron-target contacts. Prog. Neurobiol. 52: 127-144.

Rubinstein, A. L. (2003) Zebrafish: from disease modeling to drug discovery. Curr Opin Drug Discov Devel. 6: 218-223.

Sariola, H. and Saarma, M. (1999). GDNF and its receptor in the regulation of ureteric branching. Int. J. Dev. Biol. 43: 413-418.

Shentu, H., Wen, H. J., Her, G. M., Huang, C. J., Wu, J. L., Hwang, S. P. (2003) Proximal upstream region of zebrafish bone morphogenetic protein 4 promoter directs heart expression of green fluorescent protein. Genesis. 37: 103-112.

Simpson, P. B., Bacha, J. I., Palfreyman, E. L., Woollacott, A. J., McKernan, R. M., Kerby, J. (2001) Retinoic acid evoked-differentiation of neuroblastoma cells predominates over growth factor stimulation: an automated image capture and quantitation approach to neuritogenesis. Anal. Biochem. 298: 163-169.

Urtishak, K. A., Choob, M., Tian, X., Sternheim, N., Talbot, W. S., Wickstrom, E., Farber, S. A. (2003) Targeted gene knockdown in zebrafish using negatively charged peptide nucleic acid mimics. Dev. Dyn. 228: 405-413.

Westerfield. M. (1995) The Zebrafish Book, third ed., University of Oregon Press, Eugene, Oreg., USA.

Winkler, C., Schafer, M., Duschl, J., Schartl, M., Volff, J. N. (2003) Functional divergence of two zebrafish midkine growth factors following fish-specific gene duplication. Genome Res. 13: 1067-1081.

We claim:

1. A transgenic zebrafish embryo having a genome comprising:
   (a) a reporter transgene that is operatively linked to a neuron-specific promoter; and
   (b) a transgene encoding heparin-binding neurotrophic factor (HBNF) comprising the amino acid sequence set forth by SEQ ID NO: 1, wherein the HBNF-encoding transgene is operatively linked to a CMV promoter, and wherein the transgenic zebrafish embryo is capable of exhibiting a significantly enhanced neurite outgrowth expression product of the reporter transgene during development when compared to a control embryo whose genome comprises the reporter transgene operatively linked to the neuron-specific promoter and does not comprise the HBNF-encoding transgene operatively linked to the CMV promoter.

2. The transgenic zebrafish embryo of claim 1, wherein the reporter transgene encodes green fluorescent protein (GFP).

3. The transgenic zebrafish embryo of claim 1, wherein the neuron-specific promoter is HuC promoter.

4. The transgenic zebrafish embryo of claim 1, wherein the reporter transgene encodes green fluorescent protein (GFP) and the neuron-specific promoter is HuC promoter.

5. The transgenic zebrafish embryo of claim 1, wherein the reporter transgene and the HBNF-encoding transgene are in a single construct.

6. The transgenic zebrafish embryo of claim 5, wherein the reporter transgene encodes green fluorescent protein (GFP) and the neuron-specific promoter is HuC promoter.

7. The transgenic zebrafish embryo of claim 1, wherein the reporter transgene and the HBNF-encoding transgene are in separate constructs.

8. The transgenic zebrafish embryo of claim 7, wherein the reporter transgene encodes green fluorescent protein (GFP) and the neuron-specific promoter is HuC promoter.

9. A method for identifying a compound that affects neurite outgrowth comprising the steps of:
(a) exposing the transgenic zebrafish embryo of claim 1 to a test compound;
(b) detecting the neurite outgrowth expression product of the reporter transgene during development of the embryo exposed to the test compound; and
(c) comparing the pattern of the neurite outgrowth expression product of the reporter transgene expression in the embryo of claim 1 exposed to the test compound with the pattern of the neurite outgrowth expression product of the reporter transgene expression in the embryo of claim 1 not exposed to the test compound to determine whether the test compound affects the neurite outgrowth.

10. A method for identifying a compound that affects neurite outgrowth comprising the steps of:
(a) exposing the transgenic zebrafish embryo of claim 2 to a test compound;
(b) detecting the neurite outgrowth expression product of the reporter transgene during development of the embryo exposed to the test compound; and
(c) comparing the pattern of the neurite outgrowth expression product of the reporter transgene expression in the embryo of claim 2 exposed to the test compound with that in the embryo of claim 2 not exposed to the test compound to determine whether the test compound affects the neurite outgrowth.

11. A method for identifying a compound that suppresses neurite outgrowth comprising the steps of:
(a) exposing the transgenic zebrafish embryo of claim 3 to a test compound;
(b) detecting the neurite outgrowth expression product of the reporter transgene during development of the embryo exposed to the test compound; and
(c) comparing the pattern of the neurite outgrowth expression product of the reporter transgene expression in the embryo of claim 3 exposed to the test compound with that in the embryo of claim 3 not exposed to the test compound to determine whether the test compound suppresses the neurite outgrowth.

12. A method for identifying a compound that suppresses neurite outgrowth comprising the steps of:
(a) exposing the transgenic zebrafish embryo of claim 4 to a test compound;
(b) detecting the neurite outgrowth expression product of the reporter transgene during development of the embryo exposed to the test compound; and
(c) comparing the pattern of the neurite outgrowth expression product of the reporter transgene expression in the embryo of claim 4 exposed to the test compound with that in the embryo of claim 4 not exposed to the test compound to determine whether the test compound suppresses the neurite outgrowth.

* * * * *